(12) United States Patent
Ikeda et al.

(10) Patent No.: US 6,992,223 B2
(45) Date of Patent: Jan. 31, 2006

(54) METHOD FOR PRODUCING 2-BENZYLANILINE

(75) Inventors: Shin Ikeda, Haramachi (JP); Yasuhiro Takahashi, Haramachi (JP)

(73) Assignee: Konica Minolta Chemical Co.,Inc., Tokyo (JP)

( * ) Notice: Subject to any disclaimer, the term of this patent is extended or adjusted under 35 U.S.C. 154(b) by 0 days.

(21) Appl. No.: 10/515,974

(22) PCT Filed: May 28, 2003

(86) PCT No.: PCT/JP03/06707

§ 371 (c)(1),
(2), (4) Date: Nov. 23, 2004

(87) PCT Pub. No.: WO03/101930

PCT Pub. Date: Dec. 11, 2003

(65) Prior Publication Data

US 2005/0165255 A1    Jul. 28, 2005

(30) Foreign Application Priority Data

May 30, 2002  (WO) .................. PCT/JP02/05298

(51) Int. Cl.
*C07C 211/46* (2006.01)
(52) U.S. Cl. .................................... 564/315
(58) Field of Classification Search ............... 564/315
See application file for complete search history.

(56) References Cited

FOREIGN PATENT DOCUMENTS

JP    2001-199904    7/2001

*Primary Examiner*—Samuel Barts
(74) *Attorney, Agent, or Firm*—Lucas & Mercanti LLP

(57) ABSTRACT

2-benzylaniline can be manufactured in one-pot reaction at a substantially reduced cost by allowing 2-amino-5-halogenobenzophenone to react under a reductive condition.

10 Claims, 1 Drawing Sheet

METHOD FOR PRODUCING 2-BENZYLANILINE

FIELD OF THE INVENTION

The present invention relates to a new method of manufacturing 2-benzylaniline which is an important intermediate for pharmaceuticals.

BACKGROUND OF THE INVENTION 2-benzylaniline is an important compound as an intermediate material for pharmaceuticals. One of the known methods of manufacturing this compound is to reduce 2-aminobenzophenone with metallic sodium or hydrazine (J. Chem. Soc., 292, 1948; Chem. Ber., 96, 765, 1963). However, the starting 2-aminobenzophenone used therefor is difficult to obtain, and further, the cost of 2-aminobenzophenone is relatively high. Therefore, there has been a demand to develop a less expensive manufacturing method for industrial use.

Another method is known which applies Friedel-Crafts reaction-to 2-aminobenzylchloride hydrochloride and benzene by using aluminum chloride (Chem. Ber., 61, 2276, 1928). Another known method is to reduce o-nitrodiphenyl methane obtained by Friedel-Crafts reaction using 2-nitrobenzylchloride and benzene with aluminum chloride (J. Am. Chem. Soc., 53, 1428, 1931). However, benzene is a carcinogenic material and its safety problem remains unsolved in industrial production.

SUMMARY OF THE INVENTION

An object of the present invention is to provide a new and industrially advantageous method of manufacturing 2-benzylaniline.

To solve the aforementioned problems, the present inventors have made a strenuous effort and have found out a method of simultaneously performing dehalogenation and hydrogenation of a carbonyl group under a reductive condition. The method uses 2-amino-5-halogenobenzophenone as a starting material which is less expensive and easily obtainable.

Generally, in the dehalogenation reaction by catalytic reduction, basic conditions are used to promote the reaction. In hydrogenation of a carbon-oxygen bond, for example, in the case of benzophenone, the reaction is inhibited at the phase of benzhydrol under basic conditions. Acidic conditions must be used in order to promote the reaction and to reduce benzhydrol to methylene. As a result, normally, dehalogenation and hydrogenation of a carbon-oxygen bond must be carried out in two stages: under basic conditions and under acidic conditions.

The present inventors have found out that catalytic reduction to methylene by hydrogenation of a carbon-oxygen bond and dehalogenation proceed at one time, starting from 2-amino-5-halogenobenzophenone under basic conditions where catalytic reduction (hydrogenation) to methylene cannot normally be expected, or under neutral conditions (which indicate the conditions without intentionally adding an acid for hydrogenation of a carbon-oxygen bond). It is surprising that these two different reactions occur simultaneously under a reductive condition from 2-amino-5-halogenobenzophenone using a palladium or a palladium/carbon catalyst with hydrogen, and 2-benzylaniline is obtained in high yield in one-pot reaction.

In the manufacturing method of the present invention, although there coexist 2-aminobenzophenone as a dehalogenated product, 2-amino-5-halogenobenzhydrol obtained by reduction of a carbonyl group, 2-aminobenzhydrol obtained in further advanced stage of reduction and 2-amino-5-halogenobenzophenone as a reaction intermediate, they are fully reduced to 2-benzylaniline and 2-benzylaniline is obtained in high yield.

To be more specific, the method according to the present invention provides:

(1) A method of manufacturing 2-benzylaniline, wherein 2-amino-5-halogenobenzophenone is reacted under a reductive condition.

(2) The method of manufacturing 2-benzylaniline described in the aforementioned method (1), wherein an organic solvent or a water-containing organic solvent is used as a solvent for the reaction.

(3) The method of manufacturing 2-benzylaniline described in the aforementioned method (1) or (2), wherein the reaction is carried out under a reductive condition using a palladium catalyst.

(4) The method of manufacturing 2-benzylaniline described in the aforementioned method (3), wherein a base is added.

(5) The method of manufacturing 2-benzylaniline described in the aforementioned method (3), wherein an amphoteric compound is further added.

(6) The method of manufacturing 2-benzylaniline described in the aforementioned method (1), wherein a palladium-carbon catalyst in dimethylformamide is used in the reaction.

(7) The method of manufacturing 2-benzylaniline described in the aforementioned method (6), wherein a base is added.

DESCRIPTION OF THE PREFERRED EMBODIMENT

Figure 1:
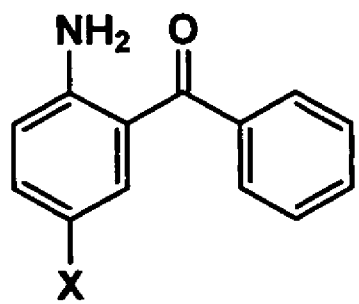
FIG. 1 shows 2-amino-5-halogenobenzophenone (where X denotes a halogen atom)
Figure 2:
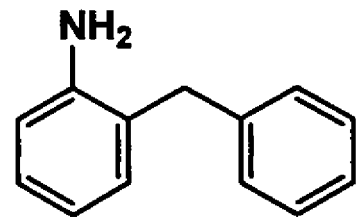
FIG. 2 shows 2-benzylaniline.

The reaction of the present invention is carried out by adding a reducing agent after mixing a starting material and a solvent, and if required, additionally mixing a base or an amphoteric compound. An organic solvent is used for extraction, then the extract is washed with water and concentrated, whereby crude 2-benzylaniline is obtained. It is purified, if required, by distillation under a reduced pressure (or purified by recrystallization or by other appropriate methods), whereby pure 2-benzylaniline can be produced.

When an organic solvent is used, an aprotic solvent such as dimethylformamide and N-methylpyrrolidone, an ether type solvent such as tetrahydrofuran and diglyme, an alcohol type solvent such as ethanol and 2-propanol, and a hydrocarbon solvent such toluene and xylene are utilized. A solution consisting the mixture thereof can also be used. Preferably used are, dimethylformamide, N-methylpyrrolidone and tetrahydrofuran because of their excellent solubility for 2-amino-5-halogenobenzophenone. Among them, dimethylformamide is more preferably used. The amount of a solvent to be used is 1 through 50-fold volume, preferably 2 through 10-fold volume, more preferably 5-fold volume with respect to the weight of 2-amino-5-halogenobenzophenone. Water may be added to improve the solubility of a salt with hydrochloride generated by the reaction. Its amount of use is 0.1 through 20-fold volume, preferably 0.5 through 5-fold volume, and more preferably 2-fold volume.

From the viewpoint of industrial production, a hydrogenation reaction is preferably used as a reductive condition because it does not produce a waste product. The catalyst used for the hydrogenation reaction is preferably a palladium catalyst, more preferably a palladium/carbon catalyst. The amount of catalyst to be used is 0.1 through 50 percent by weight, preferably 0.5 through 10 percent by weight, and more preferably 1 through 7.5 percent by weight, with respect to the weight of 2-amino-5-halogenobenzophenone. If it is less than 0.1 percent, the reaction will be too slow. If it is over 50 percent, the cost will be too high.

When a catalyst is used for hydrogenation, pressurized hydrogen conditions are preferred in order to reduce reaction time, although reaction will take place under an atmospheric pressure. The hydrogen pressure is 0.1 through 15 MPa, preferably 0.5 through 10 MPa and more preferably 1 through 5 MPa.

When hydrogenation reaction is performed, 2-benzylaniline acts as a neutralizing agent of hydrochloric acid generated during the reaction, therefore dehalogenation reaction will take place without adding a base. Since 2-amino-5-halogenobenzylaniline tends to remain at the end of the reaction, a base may be added. The preferred base includes an inorganic base such as alkaline metallic hydroxide and alkaline metallic carbonate, and an organic base such as alkaline metallic acetate, triethylamine, N-methyl morpholine and pyridine. More preferred base includes potassium carbonate and triethylamine. The amount of the base to be used is 0.1 through 1.0 mole equivalent with respect to 2-amino-5-halogenobenzophenone, preferably 0.3 through 0.9, and more preferably 0.6 through 0.8.

When more than 1.0 mole equivalent is used, the basicity of the reaction solution will be increased and the dehalogenation reaction will take place faster, however, the remaining amount of 2-aminobenzhydrol will be increased. When 2-amino-5-halogenobenzhydrol and 2-amino-5-halogenobenzylaniline as intermediates are required to eliminate completely, 1.0 mole equivalent or more of base is used. After making sure that there is almost no absorption of hydrogen, an acid component such as an acetic acid is added so that the reaction solution will be acidic, and hydrogenation is continued. Instead of base, an amphoteric compound may be used. Use of amino acid and alkylaminosulfonic acid is preferred. More preferred are alanine and taurine. The amount of the amphoteric compound to be used should be 1.0 through 10.0 mole equivalent with respect to 2-amino-5-halogenobenzophenone, and preferably 1.0 through 3.0 mole equivalent.

In the case of hydrogenation reaction, the reaction temperature is 0 through 100° C., preferably 10 through 90° C. and more preferably 20 through 60° C. The reaction time varies according to the amount of the solvent, catalyst and basic substance, hydrogen pressure and temperature. Normally, reaction time is 1 through 30 hours and generally, 3 through 6 hours. Further, in addition to the aforementioned 2-amino-5-halogenobenzylaniline, 2-amino-5-halogenobenzhydrol and 2-aminobenzhydrol as reaction intermediates tend to remain in the hydrogenation reaction under basic conditions. Accordingly, if an excessive hydrogenation reaction is carried out until they are completely reduced, aromatic nucleus will be hydrogenated, resulting in decrease of yield. Thus, the reaction is preferably terminated so that the remaining amount of the aforementioned 2-amino-5-halogenobenzylaniline, 2-amino-5-halogenobenzhydrol or 2-aminobenzhydrol will be about 0.1 through 1.5%.

The progress of reaction can be measured by chromatography with high efficiency. The liquid chromatography measuring conditions are as given below:
Column: Symmetry C18, 4.6×150 mm
Eluant: Acetonitrile/0.3% phosphate aqueous solution: 6/4
Flow rate: 1.0 ml/min.
Detector: UV 254 nm
Thermostatic bath temperature: 40° C.

EXAMPLES

The present invention will be described with reference to examples, however, the present invention is not restricted thereto.

Example 1

37.5 g of 2-amino-5-chlorobenzophenone and 188 ml of dimethylformamide were added into a 500 ml autoclave (by Hastelloy Inc.) equipped with an agitator and a thermometer, and 5.63 g of 10% palladium carbon (M type) (wet type, water: 55±5 wt %) by Kawaken Fine Chemical Inc. was then added. Air in the autoclave was replaced by nitrogen and then by hydrogen. After that, the reaction was performed at a hydrogen pressure of 3.0 MPa, a reaction temperature of 30 through 35° C. and an agitation speed of 1000 through 1100 rpm. About one hour later, the hydrogen absorption speed was reduced, and heating was applied until about 60° C. was reached. Further about one hour later, when there was almost no hydrogen absorption, cooling was carried out to reduce the temperature to the room temperature. The contents were then transferred into a 500 ml flask. The catalyst was removed by filtering with a pressure filter, and the catalyst was washed with 19 ml of dimethylformamide. Then, 200 ml of toluene, 38.8 g of 25% sodium hydroxide aqueous solution and 50 ml of water were added to the filtrate and were agitated. After that, it was transferred into a separate solution funnel, and the water layer was removed. The organic layer was washed three times with 50 ml of water. The extracted solution was concentrated under a reduced pressure and 30.1 gram of brown oil was obtained. The brown oil was subjected to distillation under a reduced pressure (0.6 KPa and 170° C.) to get 26.7 g of 2-benzylaniline.

Yield rate: 90.1%
HPLC purity: 98.7%
MS m/z=183 (molecule ion peak)
1H-NMR (CDCl3) σ3.4–3.6 (broad, 2H, —NH2), 3.9 (s, 2H, —CH2-), 6.7–7.3 (m, 9H, aromatics)

Example 2

37.5 g of 2-amino-5-chlorobenzophenone, 20.3 g of taurine and 188 ml of dimethylformamide were added into a 500 ml autoclave (by Hastelloy Inc.) equipped with an agitator and a thermometer, and 5.63 g of 10% palladium carbon (M type) (wet type, water: 55±5 wt %) by Kawaken Fine Chemical Inc. was then added. Air in the autoclave was replaced by nitrogen and then by hydrogen. After that, the reaction was performed at a hydrogen pressure of 3.0 MPa, a reaction temperature of 30 through 35° C. and an agitation speed of 1000 through 1100 rpm. About two hours later, the hydrogen absorption speed was reduced, and heating was applied until about 50° C. was reached. About another hour later, when there was almost no hydrogen absorption, cooling was carried out to reduce the temperature to the room temperature. The contents were then transferred into a 500 ml flask. The catalyst was removed by filtering with a pressure filter, and the catalyst was washed with 19 ml of dimethylformamide. Then, 200 ml of toluene, 38.8 g of 25% sodium hydroxide aqueous solution and 75 ml of water were added to the filtrate and were agitated. After that, it was transferred into a separate solution funnel, and the water layer was removed. The organic layer was washed three times with 50 ml of water. The extracted solution was concentrated under a reduced pressure and 30.7 g of brown oil was obtained. The brown oil was subjected to distillation under a reduced pressure (0.6 KPa and 170° C.) to get 27.1 g of 2-benzylaniline.

Yield rate: 91.2%

HPLC purity: 98.7%

The spectra according to the mass spectrometry and nuclear magnetic resonance spectroscopy were the same as that of the 2-benzylaniline obtained in Example 1.

Example 3

37.5 g of 2-amino-5-chlorobenzophenone, 15.8 ml of triethylamine and 188 ml of dimethylformamide were added into a 500 ml autoclave (by Hastelloy Inc.) equipped with an agitator and a thermometer, and 1.88 g of 10% palladium carbon (M type) (wet type, water: 55±5 wt %) by Kawaken Fine Chemical Inc. was then added. Air in the autoclave was replaced by nitrogen and then by hydrogen. After that, the reaction was performed at a hydrogen pressure of 3.0 MPa, a reaction temperature of 30 through 35° C. and an agitation speed of 1000 through 1100 rpm. About three hours later, the hydrogen absorption speed was reduced, and heating was applied until about 45° C. was reached. About five hours later, when there was almost no hydrogen absorption, cooling was carried out to reduce the temperature to the room temperature. The contents were then transferred into a 500 ml flask. The catalyst was removed by filtering with a pressure filter, and the catalyst was washed with 19 ml of dimethylformamide. Then, 200 ml of toluene, 19.4 g of 25% sodium hydroxide aqueous solution and 50 ml of water were added to the filtrate and were agitated. After that, it was transferred into a separate solution funnel, and the water layer was removed. The organic layer was washed three times with 50 ml of water. The extracted solution was concentrated under a reduced pressure and 29.7 g of brown oil was obtained. The brown oil was subjected to distillation under a reduced pressure (0.6 KPa and 170° C.) to get 28.0 g of 2-benzylaniline.

Yield rate: 94.6%

HPLC purity: 98.8%

The spectra according to the mass spectrometry and nuclear magnetic resonance spectroscopy were the same as that of the 2-benzylaniline obtained in Example 1.

Example 4

25.0 g of 2-amino-5-chlorobenzophenone, 8.2 g of potassium carbonate, 150 ml of dimethylformamide and 50 ml of water were added into a 500 ml autoclave (by Hastelloy Inc.) equipped with an agitator and a thermometer, and 3.75 g of 10% palladium carbon (M type) (wet type, water: 55±5 wt %) by Kawaken Fine Chemical Inc. was then added. Air in the autoclave was replaced by nitrogen and then by hydrogen. After that, the reaction was performed at a hydrogen pressure of 3.0 MPa, a reaction temperature of 30 through 35° C. and an agitation speed of 1000 through 1100 rpm. About twelve hours later, when there was almost no hydrogen absorption, cooling was carried out to reduce the temperature to the room temperature. The contents were then transferred into a 500 ml flask. The catalyst was removed by filtering with a pressure filter, and the catalyst was washed with 12 ml of dimethylformamide. Then, 130 ml of toluene, was added to the filtrate and was agitated. After that, it was transferred into a separate solution funnel, and the water layer was removed. The organic layer was washed three times with 30 ml of water. The extracted solution was concentrated under a reduced pressure and 21.0 g of brown oil was obtained. The brown oil was subjected to distillation under a reduced pressure (0.6 KPa and 170° C.) to get 16.8 g of 2-benzylaniline.

Yield rate: 85.1%

HPLC purity: 98.4%

The spectra according to the mass spectrometry and nuclear magnetic resonance spectroscopy were the same as that of the 2-benzylaniline obtained in Example 1.

Example 5

37.5 g of 2-amino-5-chlorobenzophenone, 12.3 g of potassium carbonate, 113 ml of dimethylformamide and 75 ml of water were added into a 500 ml autoclave (by Hastelloy Inc.) equipped with an agitator and a thermometer, and 5.63 g of 10% palladium carbon (M type) (wet type, water: 55±5 wt %) by Kawaken Fine Chemical Inc. was then added. Air in the autoclave was replaced by nitrogen and then by hydrogen. After that, the reaction was performed at a hydrogen pressure of 3.0 MPa, a reaction temperature of 30 through 35° C. and an agitation speed of 1000 through 1100 rpm. About seven hours later, it was confirmed that the hydrogen absorption speed was reduced, and 14 ml of acetic acid was added to continue reaction for five hours. Since there was almost no hydrogen absorption, cooling was carried out to reduce the temperature to the room temperature. The contents were then transferred into a 500 ml flask. The catalyst was removed by filtering with a pressure filter, and the catalyst was washed with 19 ml of dimethylformamide. Then, 200 ml of toluene, 38.8 g of 25% sodium hydroxide aqueous solution and 50 ml of water were added to the filtrate and were agitated. After that, it was transferred into a separate solution funnel, and the water layer was removed. The organic layer was washed three times with 50 ml of water. The extracted solution was concentrated under a reduced pressure and 28.7 g of brown oil was obtained. The brown oil was subjected to distillation under a reduced pressure (0.6 KPa and 170° C.) to get 24.1 g of 2-benzylaniline.

Yield rate: 81.4%

HPLC purity: 98.5%

The spectra according to the mass spectrometry and nuclear magnetic resonance spectroscopy were the same as that of the 2-benzylaniline obtained in Example 1.

Example 6

37.5 g of 2-amino-5-chlorobenzophenone, 15.8 ml of triethylamine and 188 ml of N-methylpyrrolidone were added into a 500 ml autoclave (by Hastelloy Inc.) equipped with an agitator and a thermometer, and 1.88 g of 10% palladium carbon (M type) (wet type, water: 55±5 wt %) by Kawaken Fine Chemical Inc. was then added. Air in the autoclave was replaced by nitrogen and then by hydrogen. After that, the reaction was performed at a hydrogen pressure of 3.0 MPa, a reaction temperature of 30 through 35° C. and an agitation speed of 1000 through 1100 rpm. About three hours later, the hydrogen absorption speed was reduced, and heating was applied until about 45° C. was reached. About two hours later, when there was almost no hydrogen absorption, cooling was carried out to reduce the temperature to the room temperature. The contents were then transferred into a 500 ml flask. The catalyst was removed by filtering with a pressure filter, and the catalyst was washed with 19 ml of N-methylpyrrolidone. Then, 200 ml of toluene, 19.4 g of 25% sodium hydroxide aqueous solution and 50 ml of water were added to the filtrate and were agitated. After that, it was transferred into a separate solution funnel, and the water layer was removed. The organic layer was washed three times with 50 ml of water. The extracted solution was concentrated under a reduced pressure and 32.1 g of brown oil was obtained. The brown oil was subjected to distillation under a reduced pressure (0.6 KPa and 170° C.) to get 27.5 g of 2-benzylaniline.

Yield rate: 92.9%

HPLC purity: 98.5%

The spectra according to the mass spectrometry and nuclear magnetic resonance spectroscopy were the same as that of the 2-benzylaniline obtained in Example 1.

Example 7

37.5 g of 2-amino-5-chlorobenzophenone, 15.8 ml of triethylamine and 188 ml of tetrahydrofuran were added into a 500 ml autoclave (by Hastelloy Inc.) equipped with an agitator and a thermometer, and 1.88 g of 10% palladium carbon (M type) (wet type, water: 55±5 wt %) by Kawaken Fine Chemical Inc. was then added. Air in the autoclave was replaced by nitrogen and then by hydrogen. After that, the reaction was performed at a hydrogen pressure of 3.0 MPa, a reaction temperature of 30 through 35° C. and an agitation speed of 1000 through 1100 rpm. About two hours later, the hydrogen absorption speed was reduced, and heating was aaplied until about 45° C. was reached. About one hour later, when there was almost no hydrogen absorption, cooling was carried out to reduce the temperature to the room temperature. The contents were then transferred into a 500 ml flask. The catalyst was removed by filtering with a pressure filter, and the catalyst was washed with 19 ml of tetrahydrofuran. Then, 200 ml of toluene, 19.4 g of 25% sodium hydroxide aqueous solution and 50 ml of water were added to the filtrate and were agitated. After that, it was transferred into a separate solution funnel, and the water layer was removed. The organic layer was washed three times with 50 ml of water. The extracted solution was concentrated under a reduced pressure and 29.5 g of brown oil was obtained. The brown oil was subjected to distillation under a reduced pressure (0.6 KPa and 170° C.) to get 27.8 g of 2-benzylaniline.

Yield rate: 93.9%

HPLC purity: 98.8%

The spectra according to the mass spectrometry and nuclear magnetic resonance spectroscopy were the same as that of the 2-benzylaniline obtained in Example 1.

Example 8

37.5 g of 2-amino-5-chlorobenzophenone, 15.8 ml of triethylamine and 188 ml of dimethylformamide were added into a 500 ml autoclave (by Hastelloy Inc.) equipped with an agitator and a thermometer, and 0.38 g of palladium black by Kawaken Fine Chemical Inc. was then added. Air in the autoclave was replaced by nitrogen and then by hydrogen. After that, the reaction was performed at a hydrogen pressure of 3.0 MPa, a reaction temperature of 30 through 35° C. and an agitation speed of 1000 through 1100 rpm. Since there was almost no hydrogen absorption about three hours later, cooling was carried out to reduce the temperature to the room temperature. The contents were then transferred into a 500 ml flask. The catalyst was removed by filtering with a pressure filter, and the catalyst was washed with 19 ml of dimethylformamide. Then, 200 ml of toluene, 19.4 g of 25% sodium hydroxide aqueous solution and 50 ml of water were added to the filtrate and were agitated. After that, it was transferred into a separate solution funnel, and the water layer was removed. The organic layer was washed three times with 50 ml of water. The extracted solution was concentrated under a reduced pressure and 30.3 g of brown oil was obtained. The brown oil was subjected to distillation under a reduced pressure (0.6 KPa and 170° C.) to get 27.0 g of 2-benzylaniline.

Yield rate: 91.2%

HPLC purity: 98.9%

The spectra according to the mass spectrometry and nuclear magnetic resonance spectroscopy were the same as that of the 2-benzylaniline obtained in Example 1.

In the Examples 1 through 8, the amount of 2-amino-5-halogenobenzylaniline, 2-amino-5-halogenobenzhydrol and 2-aminobenzhydrol in the reaction solution at the end of reaction was determined under the aforementioned chromatographic conditions. They are all within the range of 0.2 through 1.0%.

POSSIBILITY OF INDUSTRIAL APPLICATION

The manufacturing method of the present invention allows 2-benzylaniline to be manufactured in one-pot reaction without using hazardous substrates and without isolating the reaction intermediates, achieving in substantial reduction of the manufacturing cost.

What is claimed is:

1. A method of manufacturing 2-benzylaniline, comprising the step of:

allowing 2-amino-5-halogenobenzophenone to react under a reductive condition.

2. The method of manufacturing 2-benzylaniline of claim 1, wherein an organic solvent or a water-containing organic solvent is further used as a solvent for the reaction.

3. The method of manufacturing 2-benzylaniline of claim 1, wherein the reaction is carried out under the reductive condition using a palladium catalyst.

4. The method of manufacturing 2-benzylaniline of claim 3, wherein a base is further added.

5. The method of manufacturing 2-benzylaniline of claim 3, wherein an amphoteric compound is further added.

6. The method of manufacturing 2-benzylaniline of claim 1, wherein a palladium-carbon catalyst in dimethylformamide is used in the reaction.

7. The method of manufacturing 2-benzylaniline of claim 6, wherein a base is further added.

8. The method of manufacturing 2-benzylaniline of claim 2, wherein the reaction is carried out under the reductive condition using a palladium catalyst.

9. The method of manufacturing 2-benzylaniline of claim 8, wherein a base is further added.

10. The method of manufacturing 2-benzylaniline of claim 8, wherein an amphoteric compound is further added.

* * * * *